United States Patent
Kim et al.

(10) Patent No.: US 11,406,246 B2
(45) Date of Patent: Aug. 9, 2022

(54) NEEDLE-TYPE ENDOSCOPE

(71) Applicant: HAESUNG OPTICS, Hwaseong-si Gyeonggi-do (KR)

(72) Inventors: Seong Hun Kim, Hwaseong-si Gyeonggi-do (KR); Jae Son Yi, Hwaseong-si Gyeonggi-do (KR)

(73) Assignee: HAESUNG OPTICS, Hwaseong-si Gyeonggi-do (KR)

( * ) Notice: Subject to any disclaimer, the term of this patent is extended or adjusted under 35 U.S.C. 154(b) by 291 days.

(21) Appl. No.: 16/339,347

(22) PCT Filed: Nov. 2, 2017

(86) PCT No.: PCT/KR2017/012293
§ 371 (c)(1),
(2) Date: Apr. 3, 2019

(87) PCT Pub. No.: WO2018/105895
PCT Pub. Date: Jun. 14, 2018

(65) Prior Publication Data
US 2020/0037855 A1     Feb. 6, 2020

(30) Foreign Application Priority Data

Dec. 6, 2016     (KR) .......................... 10-2016-0165072

(51) Int. Cl.
A61B 17/32     (2006.01)
A61B 1/00      (2006.01)
A61B 1/05      (2006.01)

(52) U.S. Cl.
CPC ...... *A61B 1/00096* (2013.01); *A61B 1/00039* (2013.01); *A61B 1/05* (2013.01); *A61B 17/320016* (2013.01); *A61B 2017/32004* (2013.01); *A61B 2017/320052* (2013.01)

(58) Field of Classification Search
USPC ........................................................ 600/125
See application file for complete search history.

(56) References Cited

U.S. PATENT DOCUMENTS 5,159,919 A * 11/1992 Chikama ............ A61B 1/00142
                                                600/124
5,257,617 A * 11/1993 Takahashi .......... A61B 1/00142
                                                600/123

(Continued)

*Primary Examiner* — Alexandra L Newton
*Assistant Examiner* — Shankar Raj Ghimire
(74) *Attorney, Agent, or Firm* — ArentFox Schiff LLP (57) ABSTRACT

The present invention relates to a needle-type endoscope, including a camera tube having an image capturing means accommodated therein; a needle covering the camera tube from the outside and having a sharp tip formed in a front end thereof to make an incision in a human body; and a handle, wherein a length of the camera tube is formed to be longer than a length of the needle. Accordingly, it is possible to provide a needle-like endoscope configured such that a camera tube for acquiring an image is disposed inside a needle for making an incision in the human body in such a manner as to be moved forward and backward in a sliding manner inside the needle, thereby excluding constituents such as a cannula or a sheath for providing an insertion path for an endoscope, and an incision instrument.

6 Claims, 6 Drawing Sheets

(56) References Cited

U.S. PATENT DOCUMENTS

| | | | | |
|---|---|---|---|---|
| 5,385,561 | A * | 1/1995 | Cerny | A61B 17/3417 604/111 |
| 5,419,311 | A * | 5/1995 | Yabe | A61B 1/00091 600/124 |
| 5,713,870 | A * | 2/1998 | Yoon | A61B 17/3417 604/164.01 |
| 8,840,588 | B2 * | 9/2014 | Clement | A61M 13/003 604/170.01 |
| 10,463,399 | B2 * | 11/2019 | Savvouras | A61B 1/00154 |
| 2002/0165553 | A1 * | 11/2002 | Elbert | G11C 11/406 606/108 |
| 2007/0078397 | A1 * | 4/2007 | Weststrate | A61B 17/3415 604/164.01 |
| 2008/0294096 | A1 * | 11/2008 | Uber, III | A61M 31/005 604/66 |
| 2011/0313246 | A1 * | 12/2011 | Nishina | A61B 1/018 600/104 |
| 2015/0196197 | A1 * | 7/2015 | Kienzle | A61B 1/00096 600/478 |
| 2016/0235431 | A1 * | 8/2016 | Brown | A61B 17/3421 |
| 2016/0353973 | A1 * | 12/2016 | Mirza | A61B 1/00108 |
| 2018/0084974 | A1 * | 3/2018 | Wake | A61B 1/126 |
| 2018/0084986 | A1 * | 3/2018 | Ochi | A61B 1/015 |

* cited by examiner

NEEDLE-TYPE ENDOSCOPE

CROSS-REFERENCE TO RELATED APPLICATIONS

This application is a 371 U.S. national stage of PCT/KR2017/012293, filed Nov. 2, 2017 which claims the priority from Korean Patent Application No. 10-2016-0165072, filed Dec. 6, 2016, the contents of each of which are incorporated herein by reference.

TECHNICAL FIELD

The present invention relates to a needle-type endoscope.

BACKGROUND ART

An endoscope is a kind of optical instrument and largely classified into an industrial endoscope for inspecting small enclosed spaces such as pipes and ships, and a medical endoscope for inspecting inside the human body.

Among endoscopes, the medical endoscope is an apparatus for visually checking and diagnosing the inside of the human body by directly inserting the endoscope into the human body and imaging the inside. Medical endoscopes are classified into a fiberoptic endoscope and an electronic endoscope.

Here, the fiberoptic endoscope is provided in such a manner as to acquire an image by incorporating an image transmitting means such as a relay rod lens or an optical fiber in a scope inserted into a human body and disposing an image sensor on a handle that is a grip portion. In the case of such an endoscope, there is a problem that the acquisition of a high-quality image is limited due to distortion and noise in the signal transmission process.

In the meanwhile, Korean Patent Application Publication Nos. 10-2014-0065231 and 10-2012-0101450, which are related to an electronic endoscope, are configured such that an objective lens, an image sensor, and a light source are all provided at an inner end of a scope that is injected into the human body, so that a diameter of a distal end portion of the endoscope becomes large, whereby there is a problem that a severe rejection feeling occurs thus causing pain to a test subject when the endoscope is inserted into the human body.

In the prior art, a method of making an incision in the human body in a endoscope insertion portion by using an incision instrument, inserting a sheath into the incision portion, and inserting the endoscope into the sheath is performed, thus there is a problem that the pain of the test subject is increased.

DISCLOSURE

Technical Problem

Accordingly, the present invention has been made keeping in mind the above problems occurring in the prior art, and an object of the present invention is to provide an integrated needle-type endoscope configured such that a camera tube for acquiring an image is disposed inside a needle for making an incision in the human body in such a manner as to be moved forward and backward in a sliding manner inside the needle, thereby excluding constituents such as a cannula or a sheath for providing an insertion path for an endoscope, and an incision instrument.

It is another object of the present invention to provide a needle-type endoscope in which a sharp tip has an end portion provided with an inclined portion to prevent the human body from being damaged due to manipulation and displacement of the endoscope after inserting the endoscope into the human body, thereby improving safety.

It is a further object of the present invention to provide a needle-type endoscope in which a fixing projection or a fixing groove corresponding to an inclined portion is provided on one surface of the camera tube so that an inclined portion comes into contact with the fixing projection or the fixing groove as the camera tube moves forward, thereby preventing the camera tube from moving backward.

It is a further object of the present invention to provide a needle-type endoscope in which a capturing means for acquiring an image is disposed in a front end of the camera tube to realize a high-quality image and a body tube having an objective lens accommodated therein is configured to be physically supported at the rear so that the body tube accommodated in the camera tube can be prevented from being pushed backward during the assembly process or use.

Technical Solution

In order to accomplish the above object, the present invention provides a needle-type endoscope, including: a camera tube having an image capturing means accommodated therein; a needle covering the camera tube from the outside and having a sharp tip formed in a front end thereof to make an incision in a human body; and a handle, wherein a length of the camera tube is formed to be longer than a length of the needle.

Here, the camera tube may be provided in such a manner as to be moved forward and backward in a sliding manner inside the needle.

Further, the camera tube and the needle may be disposed in such a manner as to share a same concentric axis.

Here, a diameter of the needle may be formed to be equal to or less than 4 mm.

Further, a space between the needle and the camera tube may be used as a passage through which medicine or saline is supplied.

Meanwhile, in order to accomplish the above object, the present invention provides a needle-type endoscope, including: a camera tube having an image capturing means accommodated therein; a needle covering the camera tube from the outside and having a sharp tip formed on a front end thereof to make an incision in a human body; and a handle coupled to the needle having the camera tube accommodated therein, wherein a length of the camera tube is formed to be longer than a length of the needle.

Here, the camera tube and the needle may be disposed in such a manner as to share a same concentric axis, and the camera tube is provided in such a manner as to be moved forward and backward in a sliding manner inside the needle.

Further, the handle may have a top surface provided with an operation portion for allowing the camera tube to move forward and backward and an injection portion for communicating with a space between the camera tube and the needle to allow medicine or saline to be injected.

Here, the handle may have a front surface or a top surface provided with a button portion for photographing and capturing an image acquired through the camera tube.

Meanwhile, the sharp tip may have an end portion provided with an inclined portion for preventing damage due to manipulation of the endoscope after being inserted into a human body.

Here, the inclined portion may be close to or in contact with one surface of the camera tube when the camera tube moves forward.

Further, the camera tube may be provided with a fixing projection protruding on one surface thereof.

Here, the fixing projection may be provided in such a manner as to be engaged with the inclined portion in a state in which the camera tube goes past the inclined portion when moving forward thereby preventing the camera tube from moving backward.

Alternatively, the camera tube may be provided with a fixing groove recessed on one surface thereof.

Here, the fixing groove may be provided in such a manner as to be engaged with the inclined portion when the camera tube moves toward thereby preventing the camera tube from moving backward.

Advantageous Effects

According to the present invention, provided is a needle-like endoscope configured such that a camera tube for acquiring an image is disposed inside a needle for making an incision in the human body in such a manner as to be moved forward and backward in a sliding manner inside the needle, thereby excluding constituents such as a cannula or a sheath for providing an insertion path for an endoscope, and an incision instrument.

In addition, an inclined portion is provided in an end portion of a sharp tip, whereby it is possible to prevent the human body from being damaged due to manipulation and displacement of the endoscope after inserting the endoscope into the human body, thereby improving safety.

In addition, a fixing projection or a fixing groove corresponding to an inclined portion is provided on one surface of the camera tube, so that an inclined portion comes into contact with the fixing projection or the fixing groove as the camera tube moves forwards, thereby preventing the camera tube from moving backward.

In addition, a capturing means for acquiring an image is disposed in a front end of the camera tube thereby realizing a high-quality image, and a body tube having an objective lens accommodated therein is configured to be physically supported at the rear, whereby the body tube accommodated in the camera tube can be prevented from being pushed backward during the assembly process or use.

BEST MODE

Hereinafter, the configuration of the present invention will be described in detail with reference to the accompanying drawings.

Prior to the description, a detailed description of related art will be omitted if it is determined that the gist of the present invention may be unnecessarily obscured. Also, in this specification, when an element is referred to as being "connected" or "coupled" to another element, the element can be directly connected or directly coupled to the other element, but it is to be understood that the element may be connected or coupled via another component in between, unless explicitly mentioned to the contrary.

In other words, the terms used in the present specification and claims should not be construed as having a dictionary meaning, but rather a meaning the inventor deems appropriate to explain the invention in the best way. Accordingly, the present invention should be construed as meaning and concept consistent with the technical idea of the present invention.

Therefore, the embodiments shown in the present specification and the drawings are only exemplary embodiments of the present invention, and not all of the technical ideas of the present invention are described. Therefore, at the time of the present application, it should be understood that various equivalents and modifications may be present without departing from the scope of the invention.

Figure 1:
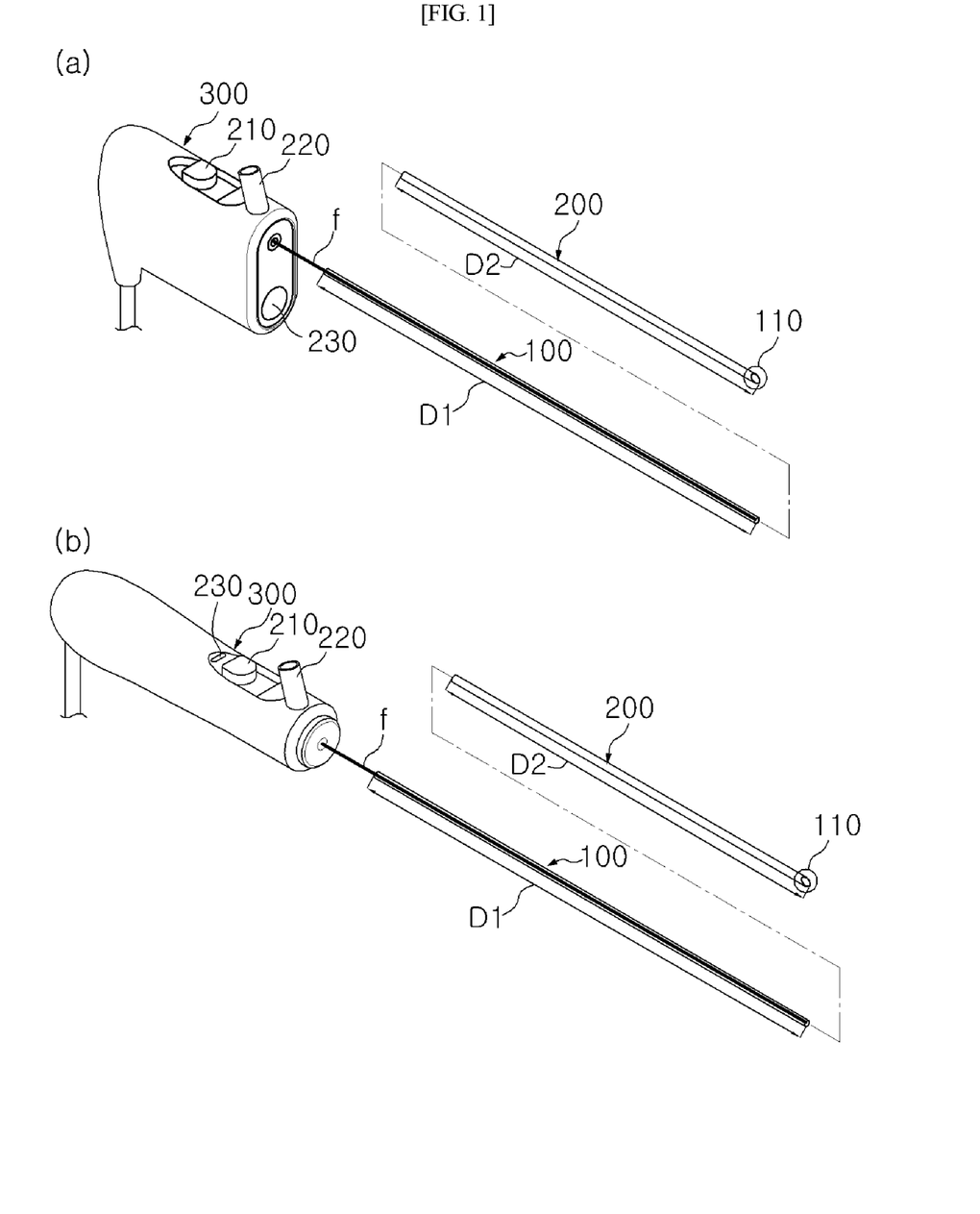
FIGS. 1(a) and 1(b) are exploded perspective views of a needle-type endoscope according to the present invention.
Figure 5:
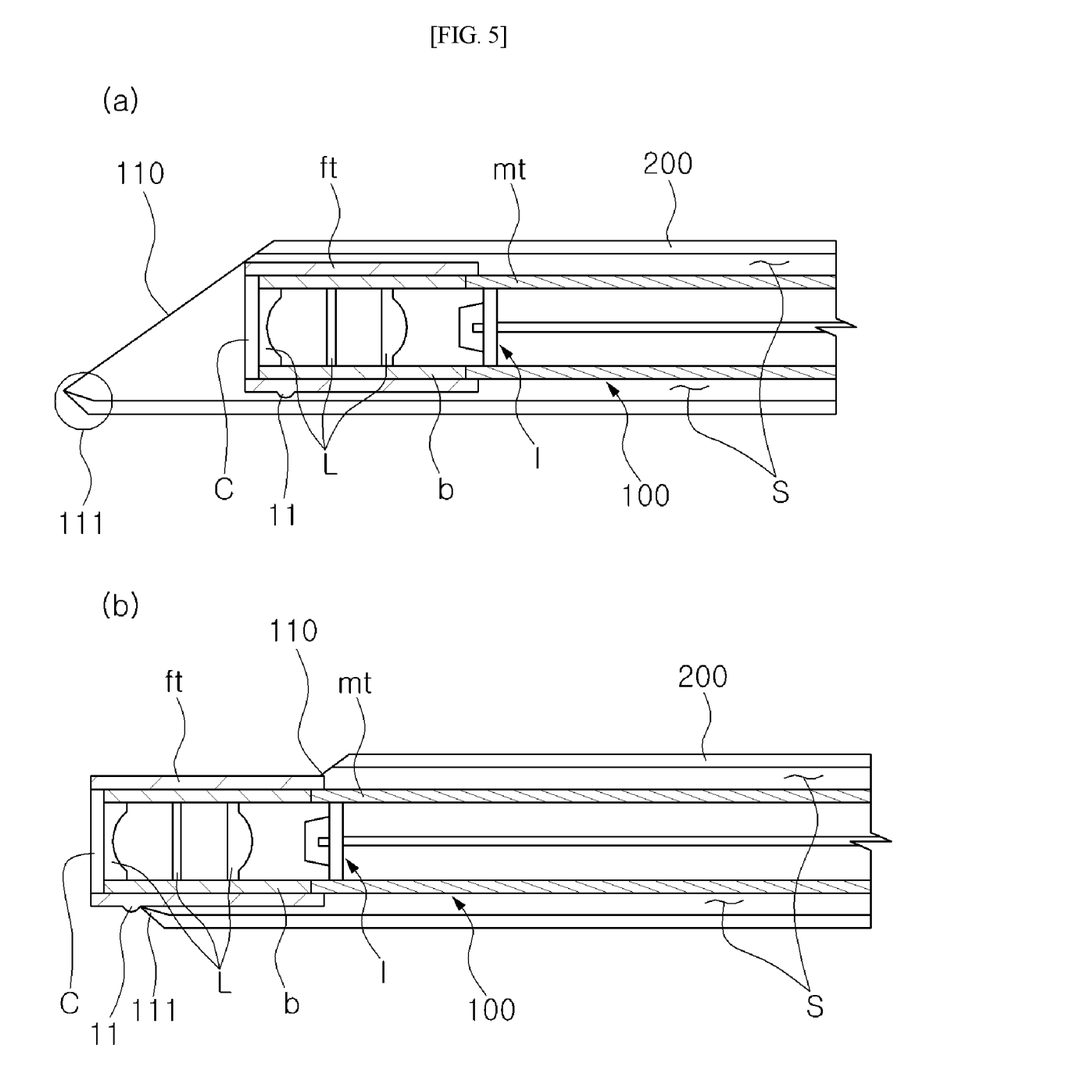
FIGS. 5(a) and 5(b) are cross-sectional views each showing a state before and after movement of a camera tube in a needle-type endoscope provided with an inclined portion and a fixing projection according to the present invention.
Figure 6:
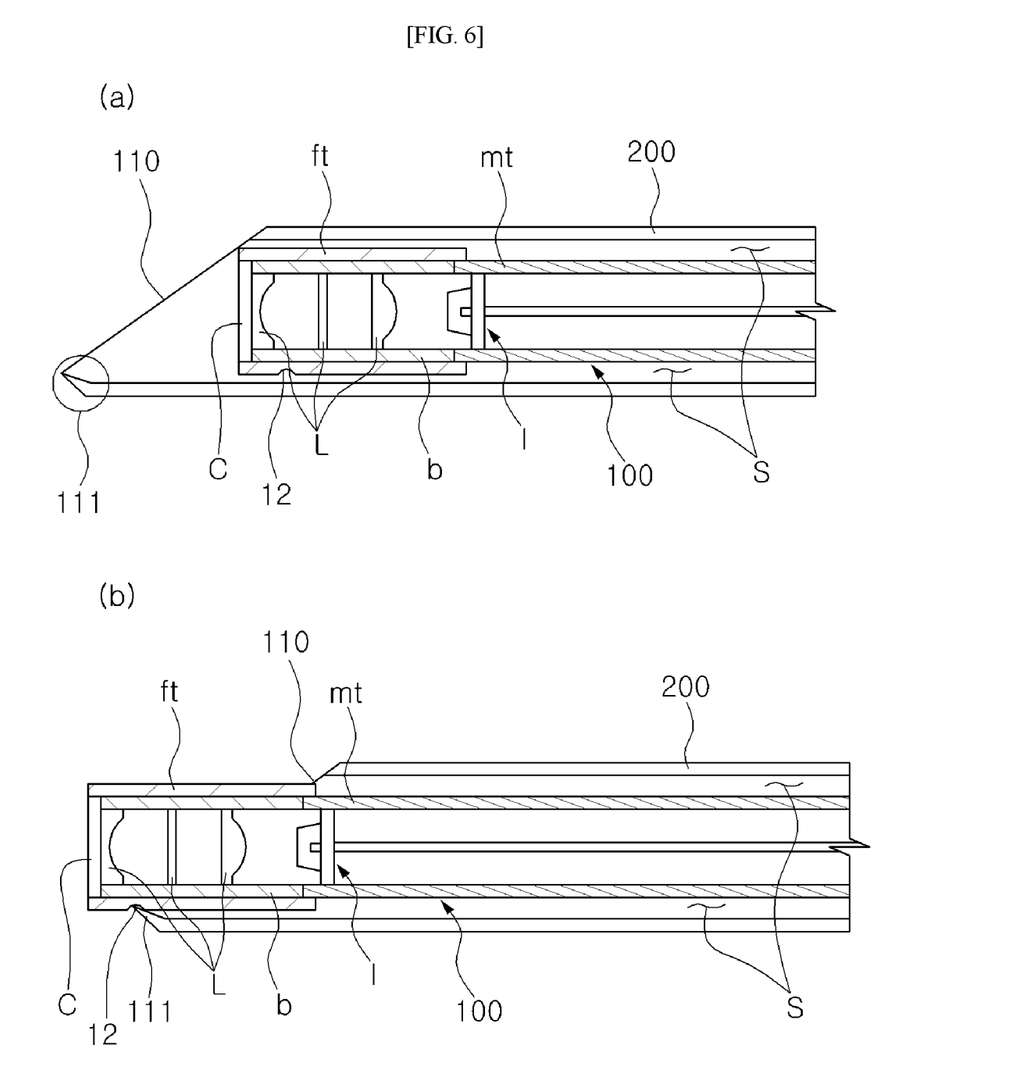
FIGS. 6(a) and 6(b) are cross-sectional views each showing a state before and after movement of a camera tube in a needle-type endoscope provided with an inclined portion and a fixing groove according to the present invention.

FIGS. 1(a) and 1(b) are exploded perspective views of a needle-type endoscope according to the present invention, FIGS. 2(a) and 2(b) are combined perspective views of a needle-type endoscope according to the present invention, FIGS. 3(a) and 3(b) are perspective views each showing a state before and after movement of a camera tube in a needle-type endoscope according to the present invention, FIGS. 4(a) and 4(b) are cross-sectional views each showing a state before and after movement of a camera tube in a needle-type endoscope provided with an inclined portion according to the present invention, FIGS. 5(a) and 5(b) are cross-sectional views each showing a state before and after movement of a camera tube in a needle-type endoscope provided with an inclined portion and a fixing projection according to the present invention, and FIGS. 6(a) and 6(b) are cross-sectional views each showing a state before and after movement of a camera tube in a needle-type endoscope provided with an inclined portion and a fixing groove according to the present invention.

Referring to FIGS. 1 to 5, a needle-type endoscope according to the present invention includes a camera tube 100 having an image-capturing means I accommodated therein, a needle 200 covering the camera tube 100 from the outside and having a front end provided with a sharp tip 110 for making an incision in a human body, and a handle 300 coupled to the needle 200 having the camera tube 100 accommodated therein.

The camera tube 100 is configured to have the image-capturing means I accommodated therein to acquire an image and to provide a space in which an optical fiber (f, including an illumination fiber for a light source and an optical fiber for image transmission) connected to the image-capturing means I is disposed, and is made of metal or synthetic resin and has an overall cylindrical structure.

The camera tube 100 includes detailed configurations of a tube body b, the object lens L fixed and supported within the tube body b, a front tube ft covering the tube body b, an image-capturing means I disposed to be adjacent to a rear portion of the tube body b, and a main tube mt covering the image-capturing means I.

Figure 4:
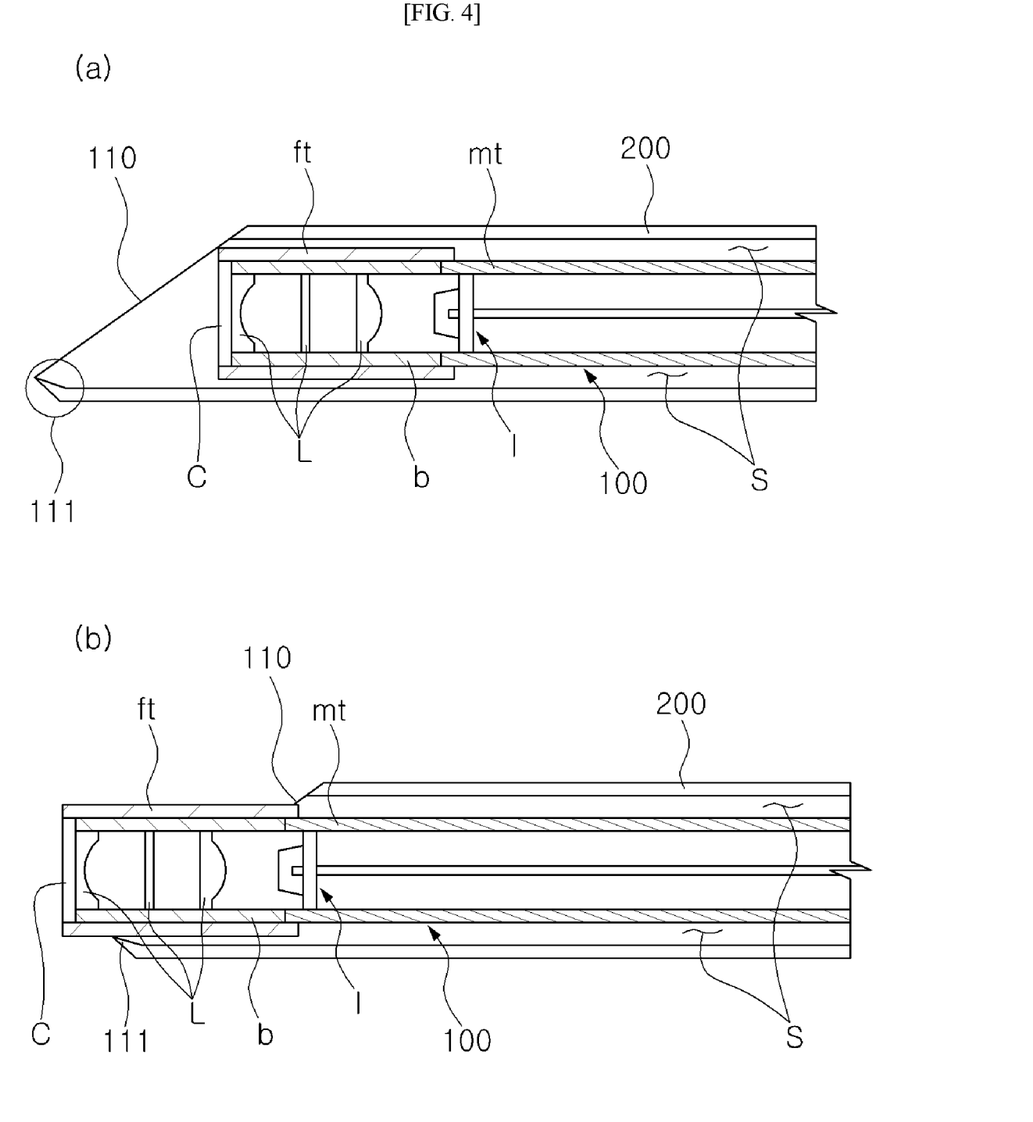
FIGS. 4(a) and 4(b) are cross-sectional views each showing a state before and after movement of a camera tube in a needle-type endoscope provided with an inclined portion according to the present invention.

As shown in FIGS. 4 and 5, the arrangement and combination relation of the detailed configurations of the camera tube 100 are provided such that the outer diameter of the front tube ft is formed to be larger than the outer diameter of the main tube mt so that the rear end of the front tube surrounds the front end of the main tube.

The length of the front tube ft is longer than the length of the tube body b, and an available space is defined at the rear end of the front tube ft according to a length relationship between the front tube ft and the tube body b and an outer diameter relationship between the front tube ft and the main tube mt, and the front end of the main tube mt is inserted in the space, whereby the tube body b is physically supported by the main tube mt, thereby preventing the tube body b from being pushed backward.

The camera tube 100 having the above-described structure is coupled to the handle 300 to be described later and moves in accordance with forward and backward movement of the operation portion 210 provided on a top surface of the handle 300.

Meanwhile, the needle 200 is configured to have a function of protecting the camera tube 100 and a function of making an incision in a human body at the same time. The needle 200 is provided to cover the camera tube 100 from the outside and to have a tip end provided with a sharp tip 110 for making an incision in the human body.

Here, the sharp tip 110 is preferably formed at an angle of 5 to 25°, and more preferably at an angle of 10 to 20°. However, the forming angle of the sharp tip 110 is not limited to those described above, and may be variously set according to the sliding distance and diameter of the camera tube 100.

In addition, the needle 200 may be made of a metal or alloy such as stainless steel, or may be made of a synthetic resin having at least a certain hardness to make an incision in the human body.

Figure 2:
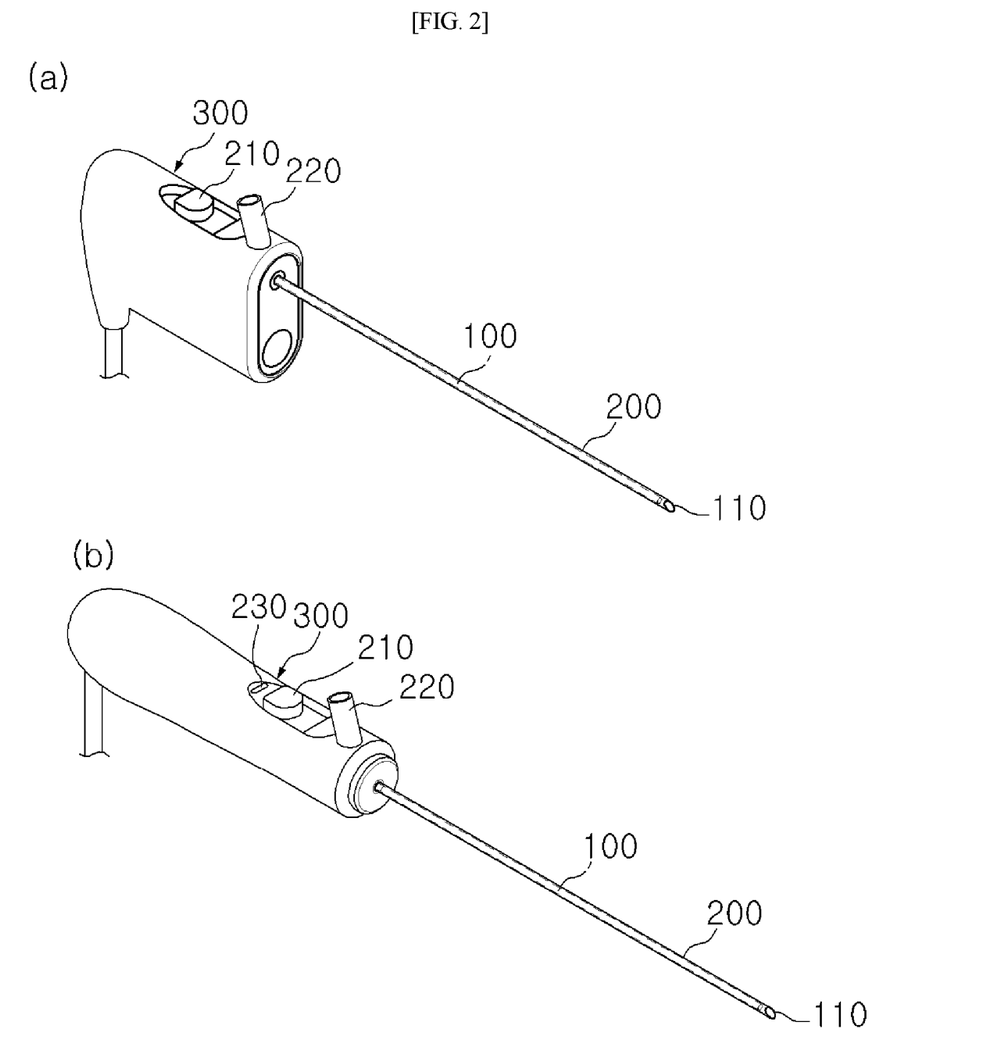
FIGS. 2(a) and 2(b) are combined perspective views of a needle-type endoscope according to the present invention.
Figure 3:
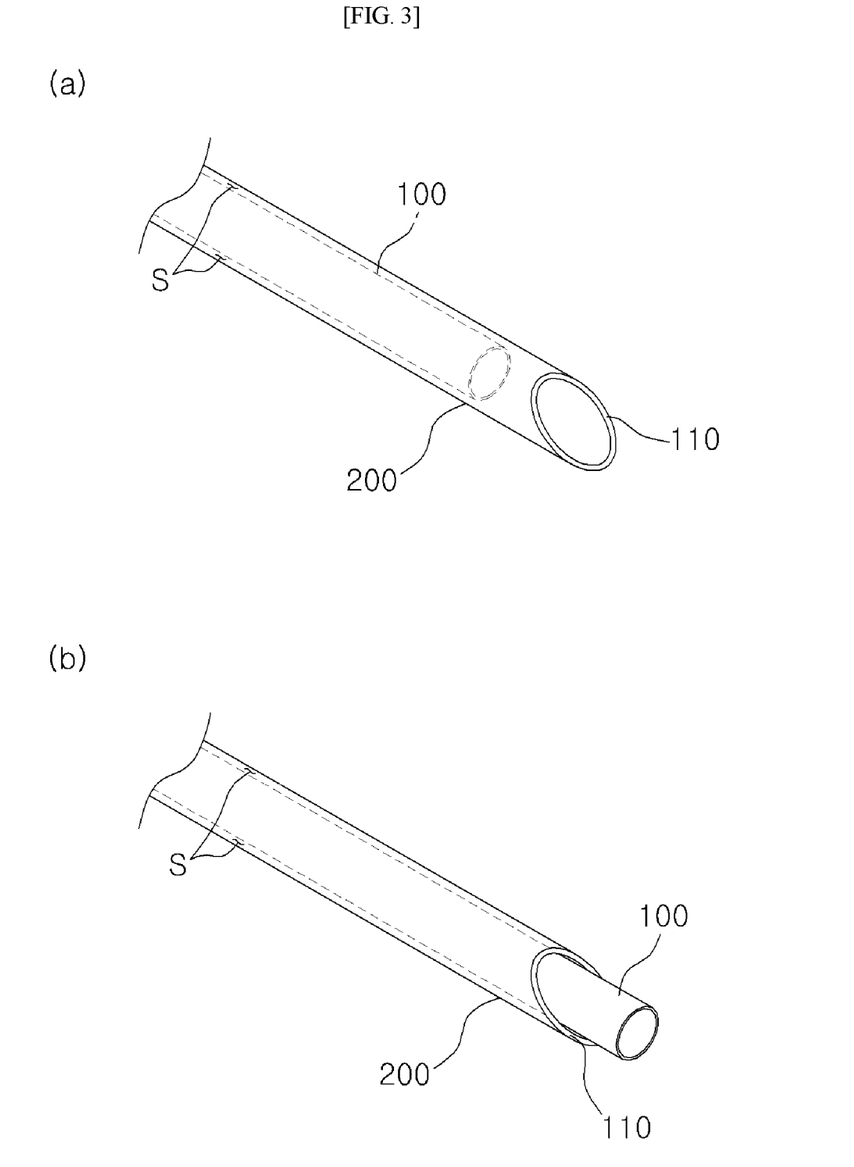
FIGS. 3(a) and 3(b) are perspective views each showing a state before and after movement of a camera tube in a needle-type endoscope according to the present invention.

Here, the length D1 of the camera tube 100 is formed to be longer than the length D2 of the needle 200. This is because the camera tube 100 needs to be drawn into the handle 300 by a predetermined length and thus physically connected to the operation portion 210 of the handle 300 in order to implement the forward and backward sliding movement of the camera tube 100. Further, the needle 300 is drawn only up to the position in which an injection portion 220 of the handle 300 is provided and fixedly coupled. Referring to FIG. 2, even though the length of the needle 200 seems to be longer than the length of the camera tube 100, the length D1 of the camera tube 100 is actually longer than the length D2 of the needle 200 because the distances by which the camera tube 100 and the needle 200 are drawn into the handle 300 are different from each other. In addition, the forward and backward sliding movement structure of the camera tube 100 is to expose all the front surface of the camera tube 100 inside the human body and thus to secure a target viewing angle, because the long side portion provided by the sharp tip 110 partially blocks the field of view of the camera tube 100.

Meanwhile, the camera tube 100 and the needle 200 are disposed to share the same center axis, which is to facilitate sliding movement of the camera tube 100 and the needle 200 not to come in contact with each other at the time of the forward and backward operations via the operation portion 210. When the camera tube 100 and the needle 200 are disposed eccentrically, the camera tube 100 and the needle 200 may come into contact with each other, in which frictional force is caused at the contact portion therebetween and thus acts as an obstacle to sliding movement.

Herein, the diameter of the needle is preferably 4 mm or less, and more preferably 2.5 mm or less.

The handle 300 is configured to provide a space in which the needle 200 having the camera tube 100 accommodated therein is coupled and a number of configurations for acquiring an image is accommodated and to serve as a grip portion operable by an inspector. The handle 300 may be provided to have a form of a gun type in which the button portion 230 is provided on a front surface thereof as shown in FIGS. 1(a) and 2(a), and a form of a pen type in which a button portion 230 is provided on a top surface thereof as shown in FIGS. 1(b) and 1(b).

The handle 300 is made of a synthetic resin material or a metal material, and is provided to form a grip portion during endoscopic treatment and include a number of components for acquiring, processing, and transmitting an image. Specifically, the handle 300 may include a plurality of operation buttons for acquiring an image and a cable for signal transmission on the outer surface thereof. In addition, the handle 300 includes an image signal processor (ISP) for processing the image that is focused onto the image sensor and transmitted through the optical fiber, an LED for providing a light source, a plurality of optical fibers (f, an optical fiber for image acquisition and an optical fiber for providing illumination) connected to the camera tube for image transmission and light source transmission, a USB port for signal transmission to the outside, a holder and a printed circuit board for supporting and electrically connecting the above-described structures, and the like.

In addition, the handle 300 has a top surface provided with the operation portion 210 that allows the camera tube 100 to move forward and backward and the injection portion 220 that is communicated with a space S between the camera tube 100 and the needle 200 for injecting medicine or saline, and the handle 300 has a front surface or a top surface provided with the button portion 230 for photographing and capturing the image acquired through the camera tube 100. Herein, the medicine or saline supplied through the injection portion 220 is supplied to the inside of the human body through the space S between the camera tube 100 and the needle 200 as a delivery passage, in which the saline is used for wiping off foreign materials attached to the front surface of the camera tube 100. In addition, the injection portion 220 may be preferably provided to be inclined at an angle from the top surface of the handle 300 not to obstruct the view or operation range of the inspector even in a state that the injection mechanism for supplying the medicine or saline is provided in the handle 300.

The needle-like endoscope structured as described above is inserted to make an incision in the human body in the state shown in FIG. 3(a). When the endoscope is inserted up to the examination position, the front surface of the camera tube 100 is exposed to the outside of the needle 200 by moving the operation portion 210 forward in order to perform inspection as shown in FIG. 3(b).

Meanwhile, the sharp tip 110 has an end portion provided with an inclined portion 111 for preventing the human body from being damaged due to manipulation of the endoscope after inserting the endoscope into the human body. The inclined portion 111 may be provided to be close to or in contact with one surface of the camera tube 100 when the camera tube 100 moves toward.

Specifically, the needle-type endoscope with the inclined portion 111 is inserted into the human body while making an incision in the human body as shown in FIG. 4(a), and the inclined portion 111 is close to or in contact with the bottom surface of the camera tube 100 when the camera tube 100 moves forward as shown in FIG. 4(b). Accordingly, it is possible to prevent the sharp tip 110 from damaging the human body even if the endoscope is displaced inside the human body, thereby enhancing the safety in use and operation of the endoscope.

In addition, the camera tube 100 may be provided with a fixing projection 11 protruding on one surface thereof, in which the fixing projection 11 is provided in such a manner as to be engaged with the inclined portion 111 in a state in which the camera tube 100 goes past the inclined portion 111 when moving forward thereby preventing the camera tube 100 from moving backward, as shown in FIG. 5(b).

Alternatively, the camera tube 100 may be provided with a fixing groove 12 recessed on one surface thereof, in which the fixing groove 12 may be provided such that the inclined portion 111 is engaged with the fixing groove 12 in a state in which the camera tube 100 moves forward, thereby preventing the camera tube 100 from moving backward, as shown in FIG. 6(b).

Preventing the camera tube 100 from moving backward may be implemented by using the inclined portion 111, the fixing projection 11, and the fixing groove 12, and also implemented by adding a displacement locking means (not shown) to the operation portion 210. For example, a fastening means such as a hook is installed in the operation portion 210 and the fastening means is engaged with the groove when the operation portion 210 is moved forward, whereby the operation portion 210 may be prevented from being displaced (and thus the camera tube is prevented from being displaced when the operation portion is prevented from being displaced because the operation portion and the camera tube are associated with each other).

The needle-like endoscope as described above may be manufactured as a disposable product requiring no washing and sterilization. When the camera tube 100 and the needle 200 are provided to be attachable to and detachable from the handle 300, only the camera tube 100 and the needle 200 that are inserted into the human body may be manufactured as disposable products.

In addition, referring to FIGS. 1 to 5, in order to clearly illustrate the features of the present invention, the moving distance of the camera tube 100, the forming angle of the sharp tip 110, the inclination angle of the inclined portion 111, and the forward protruding state of the camera tube 100 are shown in such a manner as to be somewhat exaggerated.

As described above, according to the present invention, it is possible to provide a needle-like endoscope configured such that a camera tube for acquiring an image is disposed inside a needle for making an incision in the human body in such a manner as to be moved forward and backward in a sliding manner inside the needle, thereby excluding constituents such as a cannula or a sheath for providing an insertion path for an endoscope, and an incision instrument.

In addition, an inclined portion is provided in an end portion of a sharp tip, whereby it is possible to prevent the human body from being damaged due to manipulation and displacement of the endoscope after inserting the endoscope into the human body, thereby improving safety.

In addition, a fixing projection or a fixing groove corresponding to an inclined portion is provided on one surface of the camera tube, so that an inclined portion comes into contact with the fixing projection or the fixing groove as the camera tube moves forwards, thereby preventing the camera tube from moving backward.

In addition, a capturing means for acquiring an image is disposed in a front end of the camera tube thereby realizing a high-quality image, and a body tube having an objective lens accommodated therein is configured to be physically supported at the rear, whereby the body tube accommodated in the camera tube can be prevented from being pushed backward during the assembly process or use.

While the present invention has been described with reference to the exemplary embodiments and the drawings, it is to be understood that the technical scope of the present invention is not limited to these embodiments and various changes and modifications may be made by those skilled in the art. Various modifications and variations may be made without departing from the scope of the present invention.

INDUSTRIAL APPLICABILITY

The present invention can be widely used for various kinds of endoscopes.

The invention claimed is:

1. A needle-type endoscope comprising:
   a camera tube having an image capturing means accommodated therein;
   a needle covering the camera tube from the outside and having a sharp tip (110) formed on a front end thereof to make an incision in a human body; and
   a handle coupled to the needle having the camera tube accommodated therein,
   wherein,
   a length of the camera tube is formed to be longer than a length of the needle;
   the sharp tip (110) has an end portion provided with an inclined portion (111) for preventing damage due to manipulation of the endoscope after being inserted into a human body;
   the inclined portion (111) is close to or in contact with one surface of the camera tube 100 when the camera tube (100) moves forward;
   the needle has a straight cylindrical body from the sharp tip on one end to said handle on the other end;
   the camera tube is provided with a fixing projection protruding on one surface thereof,
      wherein the fixing projection is provided in such a manner as to be engaged with the inclined portion in a state in which the camera tube goes past the inclined portion when moving forward thereby preventing the camera tube from moving backward;
      the sharp tip is bent and inclined towards the central axis of the needle; and
      said inclined portion (111) includes a first straight inclined portion and a second straight inclined portion which meet at a common vertex.

2. The needle-type endoscope of claim 1, wherein the camera tube is provided with a fixing groove recessed on one surface thereof.

3. The needle-type endoscope of claim 2, wherein the fixing groove is provided in such a manner as to be engaged with the inclined portion when the camera tube moves forward thereby preventing the camera tube from moving backward.

4. The needle-type endoscope of claim 1, wherein the camera tube and the needle are disposed in such a manner as to share a same concentric axis, and the camera tube is provided in such a manner as to be moved forward and backward in a sliding manner inside the needle.

5. The needle-type endoscope of claim 4, wherein the handle has a top surface provided with an operation portion for allowing the camera tube to move forward and backward and an injection portion for communicating with a space between the camera tube and the needle to allow medicine or saline to be injected.

6. The needle-type endoscope of claim 5, wherein the handle has a front surface or a top surface provided with a button portion for photographing and capturing an image acquired through the camera tube.

* * * * *